United States Patent [19]
Sakurai et al.

[11] Patent Number: 5,903,334
[45] Date of Patent: May 11, 1999

[54] OPHTHALMOLOGIC APPARATUS AND OPHTHALMOLOGIC-DATA MANAGEMENT SYSTEM FOR IDENTIFYING A TYPE OF MEASURING INSTRUMENT FROM OPHTHALMOLOGIC DATA AND MANAGING OPHTHALMOLOGIC DATA ACCORDING TO MEASURING INSTRUMENT TYPE

[75] Inventors: Akio Sakurai; Hisashi Tsukada; Takeshi Suzuki; Nobusuke Obata; Jun Suehiro, all of Tokyo, Japan

[73] Assignee: Kabushiki Kaisha Topcon, Tokyo, Japan

[21] Appl. No.: 08/872,182

[22] Filed: Jun. 10, 1997

[30] Foreign Application Priority Data

Jun. 11, 1996 [JP] Japan ................................ 8-148849

[51] Int. Cl.⁶ ............................................. A61B 3/00
[52] U.S. Cl. ........................................ 351/200; 351/205
[58] Field of Search ......................... 351/200, 205, 351/206, 212, 224

[56] References Cited

U.S. PATENT DOCUMENTS 5,414,478  5/1995  van Gelderen ........................ 351/205

*Primary Examiner*—Huy Mai
*Attorney, Agent, or Firm*—Finnegan, Henderson, Farabow, Garrett & Dunner, L.L.P.

[57] ABSTRACT

An ophthalmologic apparatus comprises a measuring instrument (1) for measuring a subject's eye and an ophthalmologic-data forming instrument (2) for forming ophthalmologic data which is obtained by adding kind data showing the kind of the measuring instrument (1) to measurement data measured by the measuring instrument (1). The ophthalmologic-data forming instrument (2) comprises a memory (2c) for storing the measurement data, a memory (2b) for storing the kind data, and a control unit (2a) for forming and outputting the ophthalmologic data from the data stored in the memories (2b, 2c).

8 Claims, 3 Drawing Sheets

OPHTHALMOLOGIC APPARATUS AND OPHTHALMOLOGIC-DATA MANAGEMENT SYSTEM FOR IDENTIFYING A TYPE OF MEASURING INSTRUMENT FROM OPHTHALMOLOGIC DATA AND MANAGING OPHTHALMOLOGIC DATA ACCORDING TO MEASURING INSTRUMENT TYPE

BACKGROUND OF THE INVENTION

The present invention relates to an ophthalmologic apparatus which outputs kind data showing the kinds of measuring instruments together with measurement data, and relates to an ophthalmologic-data management system for managing the measurement data by classifying the data by the instrument kinds.

Conventionally, an ophthalmologic apparatus is designed to measure a subject's eye by measuring means and print out measurement data (i.e., measured values). In addition, a management system has been proposed under which ophthalmologic data including ID data for identifying a subject is transferred from respective ophthalmologic instruments to the measurement data and, based on the transferred ophthalmologic data, a diagnosis and the like are made.

However, in this management system, since the ophthalmologic data transferred from the ophthalmologic instruments has no identification data for identifying the measuring instrument or the kind of the instrument, it is impossible to determine what data has been transferred or which instrument has measured and manage the ophthalmologic data by the classification of measuring instruments according to kinds and types.

SUMMARY OF THE INVENTION

It is an object of the present invention to provide an ophthalmologic apparatus which is capable of identifying the kind and type of a measuring instrument from ophthalmologic data.

It is another object of the present invention to provide an ophthalmologic-data management system which is capable of managing ophthalmologic data classified according to the kinds and types of measuring instruments.

The present invention is characterized in that an ophthalmologic apparatus comprises a measuring instrument for measuring a subject's eye and an ophthalmologic-data forming apparatus for forming ophthalmologic data in which kind data showing the kind of the measuring instrument is added to measurement data of the measuring instrument, and the kind of the measuring instrument is identified from the ophthalmologic data.

Further, the present invention is characterized in that there are provided a measuring instrument for measuring a subject's eye; a plurality of ophthalmologic instruments different in kind from each other, each including an ophthalmologic-data forming apparatus for forming ophthalmologic data in which kind data showing the kind of the measuring apparatus is added to measurement data of the measuring instrument; and a controller for inputting the ophthalmologic data output by the ophthalmologic instruments and causing the ophthalmologic data to be classified according to the types and kinds and be stored in a memory; and the ophthalmologic data is managed which is classified according to the kinds of the measuring instruments.

Furthermore, the present invention is characterized in that different measuring instruments are each provided with a management data forming instrument which comprises an ophthalmologic-data forming means for forming ophthalmologic data in which kind data of measuring instruments and additional data about, for example, the ID number of a subject are added to subject's eye measurement data output by the measuring instruments, a storing means for storing the ophthalmologic data formed by the ophthalmologic-data forming means, and an output means for outputting the ophthalmologic data stored in the storing means, and the ophthalmologic data is managed which is classified according to the kinds of the measuring instruments.

DETAILED DESCRIPTION OF THE PREFERRED EMBODIMENTS

Embodiments of an ophthalmologic-data management system according to the present invention will be described with reference to the accompanying drawings.

(First Embodiment)

Figure 1:
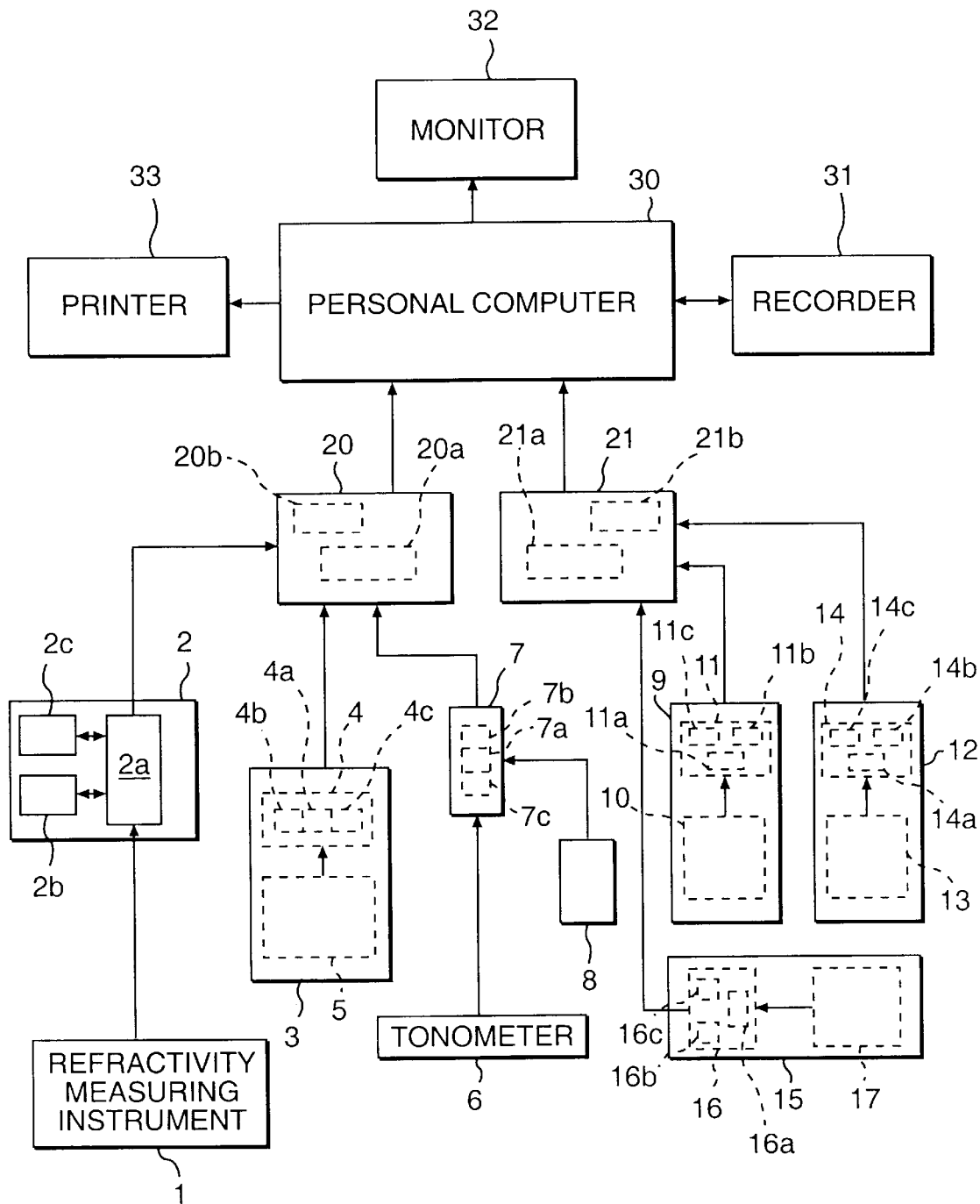
FIG. 1 is a block diagram showing a structure of an ophthalmologic-data management system according to the present invention.

An ophthalmologic-data management system shown in FIG. 1 comprises refractivity measuring instruments (measuring instruments) 1, 3 for measuring refractivity of a subject's eye, a tonometer (measuring instrument) 6 for measuring eye pressure of the subject's eye, a corneal shape measuring instrument (ophthalmologic instrument) 9, a perimeter (ophthalmologic instrument) 12, a fundus camera (ophthalmologic instrument) 15, management data forming instruments 2, 7, multiports 20, 21, a personal computer 30, a recorder 31, a monitor 32, a printer 33, and so on. An ophthalmologic instrument is composed of the refractivity measuring instrument 1 and the management data forming instrument 2. An ophthalmologic instrument is composed of the tonometer 6 and the management data forming instrument 7.

The management data forming instrument 2 forms and outputs refractivity management data (ophthalmologic data) 1D when refractivity data (measurement data) measured by the refractivity measuring instrument 1 is output.

Figure 2:
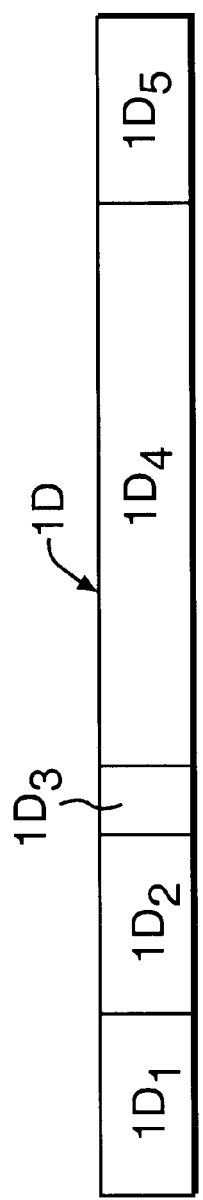
FIGS. 2(A–F) are an explanatory drawing showing a structure of management data.
Figure 2:
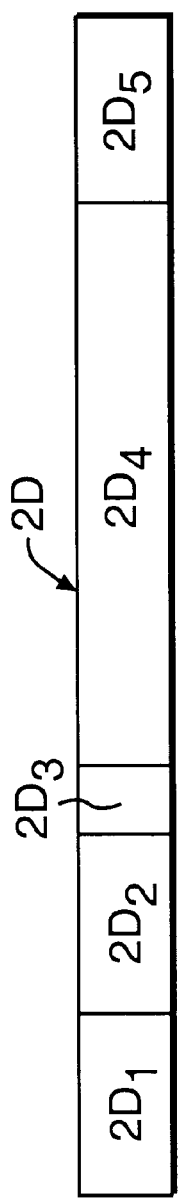
Figure 2:
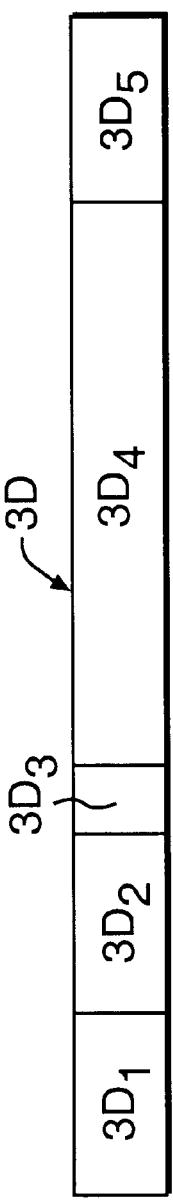
Figure 2:
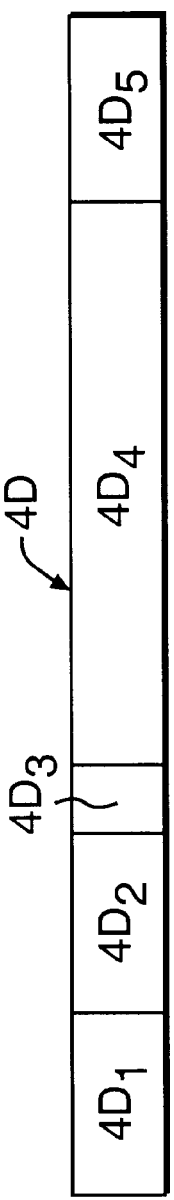
Figure 2:
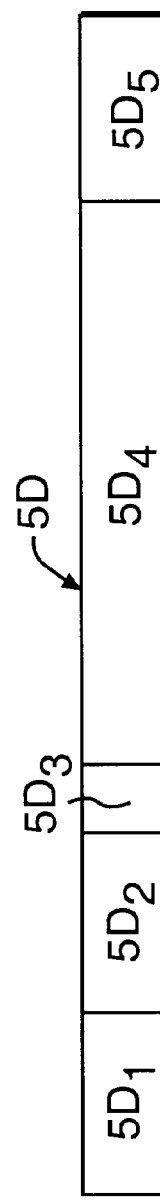
Figure 2:
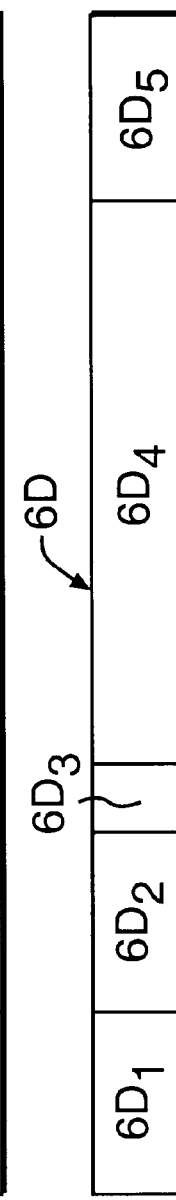

As shown in FIG. 2(A), the refractivity management data 1D comprises instrument kind data (addition data) 1D1 showing the kind of the refractivity measuring instrument (i.e., a refractivity meter, a corneal shape measuring meter, a perimeter, a tonometer, a fundus camera, and the like), instrument number data (addition data) 1D2 showing the instrument number (i.e., type number) of the instrument, serial number data (addition data) 1D3 showing measurement order, measured refractivity data (measurement data) 1D4, and ID data (addition data) 1D5 identifying a subject The respective data of the refractivity management data 1D are output from the management data forming instrument 2 in order of mention.

The ID data 1D5 and the serial number data 1D3 are input by an operator operating keys (not shown) mounted on the refractivity measuring instrument 1, and are output together with the refractivity data 1D4 from the refractivity measuring instrument 1. The ID data 1D5 may be input by bar codes instead of the keys.

The management data forming instrument 2 comprises a control unit 2a comprising a CPU and the like, a memory (second memory) 2b for storing the instrument kind data 1D1 and the instrument type data 1D2, and a memory (first memory) 2c for temporarily storing the ID data 1D5, the serial number data 1D3, the refractivity data 1D4, etc. The instrument kind data 1D1 and the instrument type number data 1D2 represent the kind and the type number of the measuring instrument connected to the ophthalmologic-data forming instrument 2, respectively. In this embodiment, the kind and the type number of the refractivity measuring instrument 1 are input to the memory 2b in advance by operating the keys (not shown) mounted on the ophthalmologic-data forming instrument 2.

The refractivity measuring instrument 3 includes a built-in management data forming instrument (ophthalmologic-data forming means) 4. As mentioned above, the management data forming instrument 4 comprises a control unit 4a comprising a CPU and the like, a memory (second memory) 4b for storing instrument kind data (addition data) 2D1 and instrument type number data 2D2 (addition data), and a memory (first memory) 4c for temporarily storing refractivity data 2D4, etc. Reference numeral 5 designates a measuring portion (measuring instrument) for measuring the refractivity of the subject's eye.

As shown in FIG. 2(B), the management data forming instrument 4 forms refractivity management data (ophthalmologic data) 2D which includes the instrument kind data 2D1 showing the kind of the refractivity measuring instrument 3, the instrument type number data 2D2 showing an instrument type number of the instrument 3, serial number data (additional data) 2D3 showing a measuring order, measured refractivity data (measurement data) 2D4, and ID data (addition data) 2D5 for identifying the subject. In order of mention, the management data forming instrument 4 outputs the respective data of the refractivity management data (ophthalmologic data) 2D.

Likewise, the ID data 2D5 and the serial number data 2D3 are input by the operator operating the keys of the refractivity measuring instrument 3. Since the instrument kind data 2D1 and the instrument type number data 2D2 have been input to the memory 4b when assembled, the operator does not need to input these data. The instrument type number data 2D2 and the instrument type number data 1D2 differ from each other in instrument type number.

The management data forming instrument 7 forms eye pressure management data (ophthalmologic data) 3D and outputs it when the tonometer 6 outputs eye pressure data (measurement data).

As shown in FIG. 2(c), the eye pressure management data 3D comprises instrument kind data (addition data) 3D1 showing the tonometer 6, instrument type number data (addition data) 3D2 showing an instrument type number, serial number data (addition data) 3D3 showing a measuring order, measured eye pressure value data (measurement data) 3D4, and ID data (addition data) 3D5 identifying the subject. The respective data of the eye pressure management data 3D are output from the management data forming instrument 7 in order of mention.

The ID data 3D5 and the serial number data 3D3 are input by the operator operating the keys (not shown) mounted on the tonometer 6, and are output together with the eye pressure value data 3D4 from the tonometer 6.

Likewise, the management data forming instrument 7 comprises a control unit 7a comprising a CPU and the like, a memory (second memory) 7b for storing the instrument kind data 3D1 and the instrument type number data 3D2, a memory (first memory) 7c for temporarily storing the ID data 3D5, the serial number data 3D3, the refractivity data 3D4, and the like. The instrument kind data 3D1 and the instrument type number data 3D2 are input the memory 7b in advance by operating the setting keys (not shown).

Reference numeral 8 designates a bar code reader for reading a bar code of an ID card (not shown) of the subject. The ID data 3D5 read by the bar code reader 8 is stored in the memory 7c of the management data forming instrument 7. If the ID data 3D5 is read by the bar code reader 8, the operator does not need to input the ID data 3D5 via the keys of the tonometer 6.

The corneal shape measuring instrument 9 comprises a measuring portion (measuring instrument) 10 for measuring the corneal shape of the subject's eye, and includes a built-in management data forming instrument 11.

Likewise, the management data forming instrument 11 comprises a control unit 11a comprising a CPU, a memory (second memory) 11b for storing instrument kind data (addition data) 4D1 and instrument type number data (addition data) 4D2, and a memory (first memory) 11c for temporarily storing configuration data (measurement data) 4D4 and the like.

As shown in FIG. 2(D), the management data forming instrument 11 forms configuration management data (ophthalmologic data) 4D which comprises the instrument kind data 4D1 showing the corneal shape measuring instrument 9, the instrument type number data 4D2 showing the instrument type number of the instrument 9, the serial number data (addition data) 4D3 showing a measuring order, the measured configuration data 4D4, and the ID data (addition data) 4D5 identifying the subject, and outputs the configuration management data 4D in order of mention.

Likewise, the ID data 4D5 and the serial number data 4D3 are input by the operator operating keys (not shown) mounted on the cornea configuration measuring instrument 9. Since the instrument kind data 4D1 and the instrument type number data 4D2 have been input to the memory 11b when assembled, the operator does not need to input these data via the keys, The perimeter 12 comprises a measuring portion (measuring instrument) 13 for measuring a visual field of the subject's eye, and has a built-in management data forming instrument 14.

Likewise, the management data forming instrument 14 comprises a control unit 14a comprising a CPU, a memory (second memory) 14b for storing instrument kind data (addition data) 5D1 and instrument type number data (addition data) 5D2, and a memory (first memory) 14c for temporarily storing visual field data (measurement data) 5D4, and the like.

As shown in FIG. 2(E), the management data forming instrument 14 forms visual field management data (ophthalmologic data) 5D which comprises the instrument kind data 5D1 showing the perimeter 12, the instrument type number data 5D2 showing the instrument type number thereof, the serial number data (addition data) 5D3 showing a measuring order, the measured visual field data 5D4, and the ID data (addition data) 5D5 identifying the subject, and outputs the respective data of the visual field management data 5D in order of mention.

Likewise, the ID data 5D5 and the serial number data 5D3 are input by the operator operating setting keys (not shown) mounted on the perimeter 12. Since the instrument kind data 5D1 and the instrument type number data 5D2 have been input to the memory 14b when assembled, the operator does not need to input these data via the setting keys A fundus camera 15 comprises a photographing portion (measuring instrument) having a CCD camera for photographing a fundus of the subject's eye, and has a built-in management data forming instrument (ophthalmologic data forming means) 16.

Likewise, the management data forming instrument 16 comprises a control unit 16a comprising a CPU, a memory (second memory) 16b for storing instrument kind data (addition data) 6D1 and instrument type number data (addition data) 6D2, and a memory (first memory) 16c for temporarily storing configuration data (measurement data) 6D4 and the like.

As shown in FIG. 2(F), the management data forming instrument 16 forms image management data (ophthalmologic data) 6D which comprises the instrument kind data 6D1 showing the fundus camera 15, the instrument type number data 6D2 showing an instrument type number of the instrument, the serial number data (addition data) 6D3 showing a measuring order, the photographic image data 6D4, and the ID data (addition data) 6D5 identifying the subject, and outputs the image management data 6D in order of mention.

Likewise, the ID data 6D5 and the serial number data 6D3 are input by the operator operating setting keys (not shown) mounted on the fundus camera 15. Since the instrument kind data 6D1 and instrument type number data 6D2 have been input to the memory 16b when assembled, the operator does not need to input these data via the setting keys.

The multiport 20 comprises a control unit 20a comprising a CPU, and a memory 20b for temporarily storing data. When the refractivity management data 1D, 2D, the eye pressure management data 3D, etc. are input at the same time, the multiport 20 causes these data 1D, 2D and 3D to be temporarily stored in the memory 20b, the management data 1D, 2D and 3D are then read from the memory 20b in order, and these management data are output to a personal computer 30 serially.

The order in which the management data 1D, 2D and 3D are read from the memory 20b is determined such that, for example, judgment is formed as to which one of the measurement data 1D4, 2D4, and 3D4 is smallest in amount among the instrument kind data 1D1, 2D2, and 3D3, and the smallest data in quantity is taken out to read.

The multiport 21 comprises a control unit 21 comprising a CPU, and a memory 21b for temporarily storing data. Since the multiport 21 has the same function as the multiport 20, a description thereof is omitted.

The personal computer 30 causes the management data 1D to 6D from the multiports 20 and 21 to be input to and stored in a storing instrument 31 with a classification based on the instrument kinds. In addition, the computer 30 causes the management data 1D to 6D stored in the storing instrument 30 to be read, be displayed on a monitor 32, and be printed out via a printer 33.

Operation in the aforementioned embodiment will be described.

First, the instrument kind and the instrument type number of the refractivity measuring instrument 1 connected to the management data forming instrument 2 are input to the memory 2b in advance by operating the setting keys (not shown) mounted on the management data forming instrument 2. Likewise, the instrument kind and the instrument type number of the tonometer 6 connected to the management data forming instrument 7 are input to the memory 7b in advance by operating the setting keys (not shown) mounted on the management data forming instrument 7.

When the refractivity of the subject's eye is measured by the refractivity measuring instrument 1, the ID code of the subject and the number showing a measuring order are first input by operating the keys mounted on the refractivity measuring instrument 1, and then, when the measurement of the refractivity by the refractivity measuring instruments is completed, the ID data 1D5 showing the ID code and the serial number data showing the number of the measuring order together with the resultant refractivity data 1D4 are output from the refractivity measuring instrument 1 and are input to the management data forming instrument 2.

The control unit 2a of the management data forming instrument 2 causes the memory 2c to store the ID data 1D5, the serial number data 1D3, the refractivity data 1D4, and the like. The control unit 2a forms and outputs the refractivity management data 1D shown in FIG. 2(A) from the data stored in the memory 2c and the data in advance stored in the memory 2b.

Since the refractivity management data 1D includes the instrument kind data 1D1 and the instrument type number data 1D2, it can be found, based on the refractivity management data 1D, which kind of instrument and which type of instrument have measured to obtain the result.

Likewise, when the refractivity of the subject's eye is measured by the refractivity measuring instrument 3, the ID code of the subject and the number showing a measuring order are first input by operating the keys mounted on the refractivity measuring instrument 3. After that, when the measurement of the refractivity by the refractivity measuring instrument 3 is completed, the resultant refractivity data 2D4 is output from the measuring portion 5 and is stored in the memory 4c of the management data forming instrument 4. The control unit 4a forms and outputs the refractivity management data 2D shown in FIG. 2(B) from the data stored in the memory 4c and the data stored in advance in the memory 4b.

Since the instrument kind and the type number of the refractivity measuring instrument 3 have been input and stored in the memory 4b, there is no need to input these data by operating the keys.

When the eye pressure of the subject's eye is measured by the tonometer 6, the ID code of the subject and the number showing a measuring order are input by operating the keys mounted on the tonometer 6. The ID code may be input by the bar code reader 8 instead of the keys. In this case, the ID data 3D5 is input into the memory 7c when the bar code written in an ID card (not shown) of the subject is read with the bar code reader 8.

When the measurement of the eye pressure by the tonometer 6 is completed, the ID data 3D5 and the serial number data 1D3 showing the number of the code measuring order are output together with the resultant eye pressure data 3D4 from the tonometer 6 and are input into the management data forming instrument 7, The control unit 7a of the management data forming instrument 7 causes the memory 7c to store the ID data 3D5, the serial number data 3D3, the refractivity data 3D4, and the like. Thereafter, the control portion 7a forms and outputs the refractivity management data 3D shown in FIG. 2(C) from the data stored in the memory 7c and the data stored in advance in the memory 7b.

Likewise, when the measurement is completed by the corneal shape measuring instrument 9 and the perimeter 12, the configuration management data 4D and the visual field management data 5D shown in FIGS. 2(D) and 2(E), respectively, are output from the corneal shape measuring instrument 9 and the perimeter 12. In addition, when the fundus of the subject eye is photographed, the image management data 6D shown in FIG. 2(F) is output from the fundus camera 15.

The multiport 20 inputs the refractivity management data 1D, 2D and the eye pressure management data 3D and outputs these data to the personal computer 30. When these data 1D to 3D are input at the same time, the control unit 20a causes the memory 20b to store the management data 1D to 3D. Thereafter, based on a predetermined priority, the control unit 20a reads the management data 1D to 3D stored in the memory 20b and outputs them to the personal computer 30 serially.

When receiving the management data 1D to 3D, the personal computer 30 classifies these data into data based on the instrument kind data 1D1 to 3D1, and further classifies the data into data based on the instrument type number data 1D2 to 3D2, and further classifies the data into data based on the subject ID data 1D5 to 3D5, and causes the recorder 31 to record the management data 1D to 3D.

Likewise, the multiport 21 inputs the management data 4D to 6D and outputs them to the personal computer 30. When these data 1D to 3D are input at the same time, the control unit 20a causes the memory 21b to store the management data 4D to 6D. Thereafter, based on the predetermined priority, the control unit 21a reads the management data 1D to 3D stored in the memory 21b and outputs them to the personal computer 30 serially.

When receiving the management data 4D to 6D, the personal computer 30 classifies the management data 4D to 6D into data based on the instrument kind data 4D1 to 6D1, and further classifies the data into data based on the instrument type number data 4D2 to 6D2, and further classifies the data into data based on the subject ID data 4D5 to 6D5, and causes the recorder 31 to store the classified management data 4D to 6D.

Since the management data 1D to 6D are thus classified by instrument kinds by instrument type numbers, and by subjects and are stored and recorded in the recorder 31, the measurement data and the subject data about the respective instruments or instrument types can be managed collectively.

Since the management data 1D to 6D include data about the instrument kinds 1, 3, 6, 9, 12, and 15 and instrument type numbers in addition to the measurement data obtained by the instruments 1, 3, 6, 9, 12, and 15, the respective measurement data can be managed even if the management data 1D to 6D are continuously output from the multiports 20, 21 in a short time.

The ophthalmologic data management system according to this embodiment is very convenient to a situation where the measuring instruments 1, 3, 6, 9, 12, and 15 are individually located in different consulting rooms. In this situation, there is no need to, for data totalization, collect floppy disks on which the data measured by the measuring instruments is stored, for example.

Additionally, even if many subjects are measured with the measuring instruments 1, 3, 6, 9, 12, and 15 in a group examination, the ophthalmologic data forming instruments 2, 4, 7, 11, 14, and 16 form and output the management data 1D to 6D including the instrument kind data 1D1 to 6D1 and the ID data 1D5 to 6D5. Accordingly, the measurement data can be managed which is classified by the subjects and, in addition, by the measuring instruments 1, 3, 6, 9, 12, and 15 and the instrument types. This is a great advantage.

In this embodiment, not only the measurement data but also the ID data and the serial number data are output from the refractivity measuring instrument 1, the tonometer 6, the measuring portions 10, 13, and the photographing portion 17. In addition to these data, date data showing a measuring date and hour may be output. In this case, the date data is included in the management data 1D to 6D.

In this embodiment, the management data forming instruments 2, 4, 7, 11, 14, and 16 output the instrument kind data 1D1 to 6D1, the instrument type number data 1D2 to 6D2, the serial number data 1D3 to 6D3, the measurement data 1D4 to 6D4, and the ID data 1D5 to 6D5 in order of mention. However, it is not necessarily required to output these data in this order.

The management data forming instrument 2 outputs the refractivity management data 1D whenever the data 1D is formed. Instead, the instrument 2 may be provided with a memory for storing the refractivity management data 1D so that the control unit 2a reads and outputs the stored refractivity management data 1D when the refractivity management data 1D is stored in the memory to a certain extent. In this case, the ophthalmologic management data forming instrument is made up of the management data forming instrument, the storing memory, and the like.

In this embodiment, the fundus camera 15 is connected to the multiport 21. Instead, a corneal endothelium photographing instrument, for example, may be connected thereto, of course.

Figure 3:
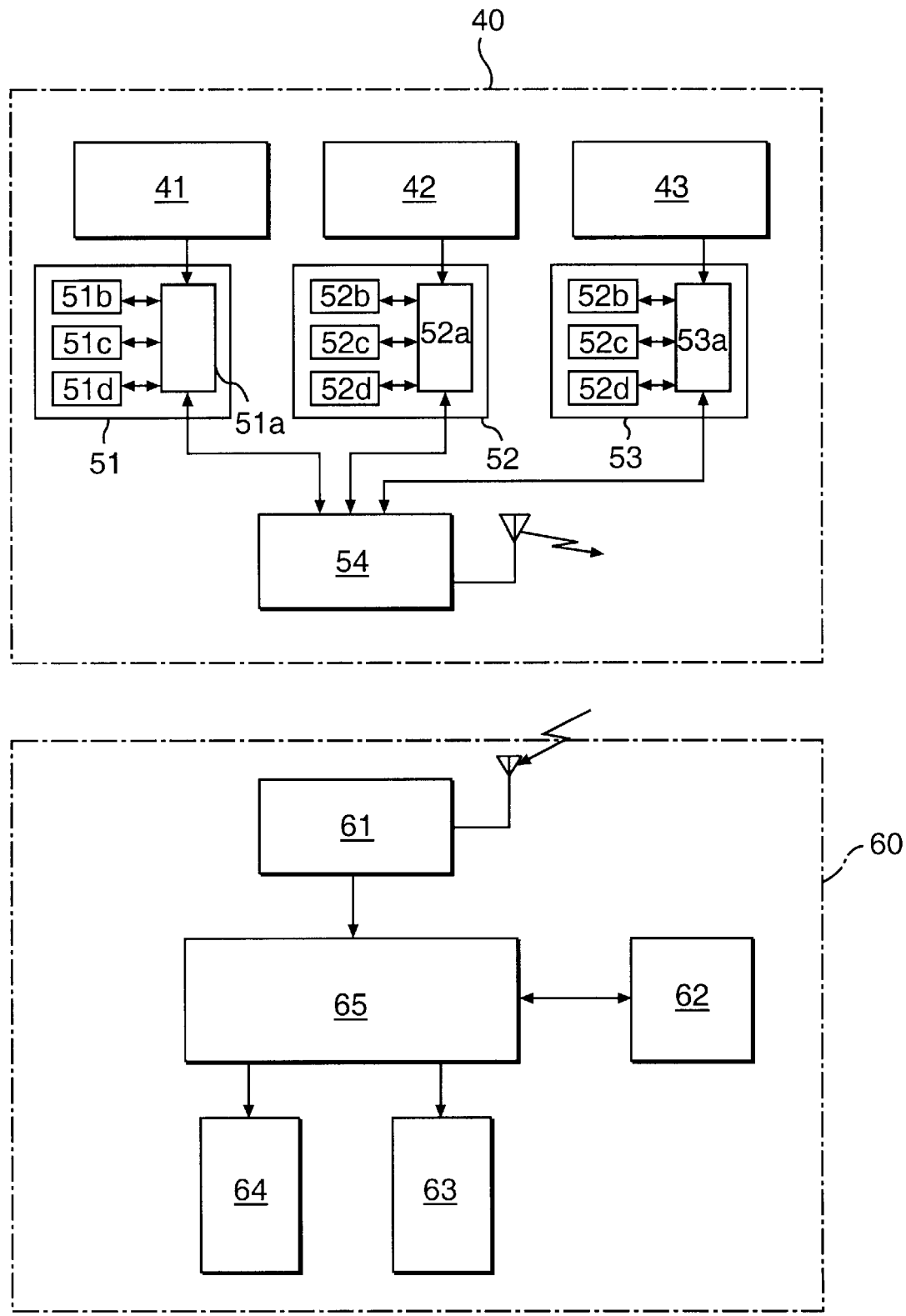
FIG. 3 is a block diagram showing a structure according to a second embodiment of the present invention.

(Second Embodiment) As shown in FIG. 3, an ophthalmologic-data management system in a second embodiment comprises a transmitting system 40 and a receiving system 60.

The transmitting system 40 comprises refractivity measuring instruments 41, 42 which differ in instrument type number from each other, a tonometer 43, management data forming instruments 51 to 53, and a transmitting portion 54. An ophthalmologic instrument is made up of the refractivity measuring instrument 41 and the management data forming instrument 51, an ophthalmologic instrument is made up of the refractivity measuring instrument 42 and the management data forming instrument 52, and an ophthalmologic instrument is made up of the tonometer 43 and the management data forming instrument 53.

The management data forming instrument 51 comprises a control unit (ophthalmologic-data forming means, outputting means) 51a comprising a CPU, a memory 51b for storing the instrument kind data 1D1 and the instrument type number data 1D2, a memory 51c for temporarily storing the ID data 1D5, the serial number data 1D3, the refractivity data 1D4 and the like, and a memory 5id for storing the ophthalmologic data 1D formed based on the data stored in the memory 51c. The ID data 1D5 and the serial number data 1D3 are input by the operator operating the keys (not shown) mounted on the refractivity measuring instrument 41.

When the refractivity measuring instrument 41 outputs the ID data 1D5 and the serial number data 1D3 together with the measured refractivity data 1D4, the control unit 51a causes the memory 51c to store the ID data 1D5, the serial number data 1D3, the refractivity data 1D4, and the like. Thereafter, the control unit 51a forms the management data 1D shown in FIG. 2(A) from the data stored in the memory 51c and the data stored in advance in the memory 51b, and causes the memory 51d to store the management data 1D.

The management data forming instruments 52 and 53 serve to form the ophthalmologic data 2D and 3D, and each have the same construction as the management data forming instrument 51. The transmitting portion 54 reads the management data stored in memories 51d to 53d and transmits the management data by wireless.

The receiving system 60 comprises a receiving portion 61 for receiving transmitted management data, a recorder 62 for recording the received management data, a monitor 63 for displaying the management data recorded in the recorder 62, a printer 64 for printing out the management data, and a personal computer 65 for managing the management data.

Operation in the second embodiment will be described.

When the subject's eye is measured with the refractivity measuring instruments 41, 42 and the tonometer 43, the management data is formed by the management data forming instruments 51, 52, 53, and is stored in the memories 51d to 53d, as in the first embodiment. Whenever the measurement is carried out, the respective management data are added and stored in the memories 51d to 53d. When the management data are stored therein to a certain extent, the management data stored in the memories 51d to 53d are read and transmitted by the transmitting portion 54.

When the transmitted management data is received by the receiving portion 61 of the receiving system 60, the personal computer 65 classifies the data by instrument kinds according to the instrument kind data 1D1 to 3D1 of the management data 1D to 3D, and further classifies the data by instrument types according to the instrument type number data 1D2 to 3D2, and further classifies the data by subjects according to the ID data 1D5 to 3D5, and causes the recorder 62 to record them.

Since the management data 1D to 3D are thus classified by instrument kinds, by instrument types, and by subjects and are stored and recorded in the recorder 62, the subject data and the measurement data about the respective instruments or instrument types can be managed collectively.

According to the second embodiment, by locating the transmitting system 40 in a consulting house and locating the receiving system 60 in a hospital, a group examination can be speedily performed in a place far away from the hospital. This is convenient especially to an examination performed in a detached island.

In the second embodiment, the management data is transmitted by wireless. Instead, telephone lines may be used for transmission. Additionally, the memories 51d to 53d may be detachably mounted so that when the management data is stored to a certain extent in the memories 51d to 53d, the memories 51d to 53d are removed and sent to the hospital by post, and the memories 51d to 53d are connected to the personal computer to read the management data.

What is claimed is:

1. An ophthalmologic apparatus comprising:
    a measuring instrument for measuring an eye of a subject; and
    an ophthalmologic-data forming instrument for forming ophthalmologic data including identifying data for identifying said measuring instrument and measurement data measured by said measuring instrument;
    wherein said measuring instrument is identified by said ophthalmologic data.

2. An opthalmologic apparatus according to claim 1, wherein said ophthalmologic-data forming instrument comprises:
    a first memory for storing said measurement data;
    a second memory for storing said identifying data; and
    a control unit for forming said ophthalmologic data from said measurement data stored in said first memory and said identifying data stored in said second memory and outputting said ophthalmologic data.

3. An ophthalmologic apparatus according to claim 2, wherein
    said first memory stores ID data for identifying a subject in addition to said measurement data;
    said identifying data stored in said second memory comprises instrument identification data and instrument number data relating to said measuring instrument; and
    said control unit outputs respective data stored in said first and second memories in predetermined order.

4. An ophthalmologic apparatus according to claim 3, wherein said first memory stores date data concerning a date and hour of measurement in addition to said measurement data and said ID data.

5. An ophthalmologic apparatus according to claim 1, wherein said identifying data includes instrument identification data and instrument number data, each relating to said measuring instrument.

6. An ophthalmologic-data management system comprising:
    a plurality of ophthalmologic apparatuses using different identifying data, each comprising:
    a measuring instrument for measuring an eye of a subject; and
    an ophthalmologic-data forming instrument for forming ophthalmologic data obtained by adding identifying data, for identifying said measuring instruments, to measurement data obtained by measuring said measuring instrument; and
    a control unit for allowing a memory to receive the ophthalmologic data output by the plurality of said ophthalmologic apparatuses and store the ophthalmologic data classified according to the identifying data of each apparatus, so that the ophthalmologic data is managed according to the identifying data of each of said ophthalmologic apparatuses.

7. An ophthalmologic-data management system comprising:
    measuring instruments using different identifying data, each including a management data forming instrument, said management data forming instrument comprising:
    ophthalmologic-data forming means for forming ophthalmologic data including measurement data measured by said measuring instruments, identifying data for identifying said measuring instruments, and addition data relating to a plurality of ID numbers of subjects;
    storing means for storing the ophthalmologic data formed by said opthalmologic-data forming means; and
    outputting means for outputting the ophthalomologic data stored in said storing means;
    wherein the ophthalmologic data is managed according to the identifying data of each of said measuring instruments.

8. An ophthalmologic-data management system according to claim 7, further comprising:
    transmitting means for transmitting the ophthalmologic data output by said outputting means;
    receiving means for receiving the ophthalomologic data;
    control means for classifying the ophthalmologic data received by said receiving means by the identifying data of said measuring instruments or the subjects, based on the identifying data and subject 1D data included in the ophthalmologic data; and
    memory means for storing the ophthalmologic data classified by said control means.

* * * * *